US010371650B2

(12) United States Patent
Li

(10) Patent No.: US 10,371,650 B2
(45) Date of Patent: Aug. 6, 2019

(54) MACROTEXTURE MAP VISUALIZING TEXTURE HETEROGENEITY IN POLYCRYSTALLINE PARTS

(71) Applicant: Dongsheng Li, Farmington, CT (US)

(72) Inventor: Dongsheng Li, Farmington, CT (US)

(73) Assignee: Advanced Manufacturing LLC, East Hartford, CT (US)

( * ) Notice: Subject to any disclaimer, the term of this patent is extended or adjusted under 35 U.S.C. 154(b) by 46 days.

(21) Appl. No.: 15/273,128

(22) Filed: Sep. 22, 2016

(65) Prior Publication Data
US 2018/0080884 A1    Mar. 22, 2018

(51) Int. Cl.
*G01N 23/203*   (2006.01)
*G06T 11/20*    (2006.01)
*G06T 11/00*    (2006.01)
*G06K 9/62*     (2006.01)
*G01N 23/2206*  (2018.01)

(52) U.S. Cl.
CPC ....... *G01N 23/203* (2013.01); *G01N 23/2206* (2013.01); *G06K 9/6218* (2013.01);
(Continued)

(58) Field of Classification Search
CPC ............. G01N 23/203; G01N 23/2206; G01N 2223/606; G01N 2223/401; G06K 9/6218; G06T 11/001; G06T 11/206
See application file for complete search history.

(56) References Cited

U.S. PATENT DOCUMENTS 4,677,576 A *  6/1987  Berlin, Jr. .............. G09B 9/301
                                              345/420
6,181,802 B1 *  1/2001  Todd ....................... G06T 9/004
                                              348/E7.024
(Continued)

OTHER PUBLICATIONS

Myagchilov et al. "Modelling and Simulation in Materials Science and Engineering", 1999 Modelling Simul. Mater. Sci. Eng. 7975. (Year: 1999).*

*Primary Examiner* — Tapas Mazumder
(74) *Attorney, Agent, or Firm* — UConn IP Law Clinic; Thomas Kennedy, III

(57) ABSTRACT

This invention provides a method, system, and computer program to visualize texture (crystal orientation distribution) heterogeneity in polycrystalline aggregate part in large length scale. This is a critical representation step for microstructure characterization, useful in effective behavior simulation, risk analysis and hotspot identification. In contrast to orientation image map where each color component represents a crystal orientation, each color in this macrotexture map represents a set of texture. Different color represent different texture and similar texture shall have similar color. This method will provide a critical tool in evaluating texture heterogeneity of components, leading to a first-hand understanding of property heterogeneity and anisotropy. For an experienced user, these maps serve the same purpose in identifying high risk locations in the investigated component as medical imaging maps do for diagnosis purpose. This method will also serve as a starting point in mesoscale simulation with meshing sensitivity based on the texture heterogeneity. It will provide a bridge between texture characterization and behavior simulation of component with texture heterogeneity. This method will also offer a linkage between crystal plasticity simulation in small length scale and finite element/difference simulation in large length scale.

12 Claims, 10 Drawing Sheets

(52) U.S. Cl.
CPC .......... *G06T 11/001* (2013.01); *G06T 11/206* (2013.01); *G01N 2223/401* (2013.01); *G01N 2223/606* (2013.01)

(56) References Cited

U.S. PATENT DOCUMENTS

| | | | | |
|---|---|---|---|---|
| 6,940,505 | B1 * | 9/2005 | Savine | G06T 17/20 345/419 |
| 2002/0101419 | A1 * | 8/2002 | Cook | G06T 15/50 345/426 |
| 2007/0209741 | A1 * | 9/2007 | Carpenter | B21B 1/0805 148/668 |
| 2009/0116749 | A1 * | 5/2009 | Cristinacce | G06K 9/00281 382/195 |
| 2009/0284772 | A1 * | 11/2009 | Sai | G01J 3/46 358/1.9 |
| 2011/0043501 | A1 * | 2/2011 | Daniel | H05B 33/0857 345/207 |
| 2012/0219195 | A1 * | 8/2012 | Wu | A61B 5/04007 382/128 |
| 2017/0243364 | A1 * | 8/2017 | Carmi | G06T 7/45 |

* cited by examiner (a)

(b)

MACROTEXTURE MAP VISUALIZING TEXTURE HETEROGENEITY IN POLYCRYSTALLINE PARTS

REFERENCES CITED

D. S. Li. Review of structure representation and reconstruction on mesoscale and microscale. JOM. 2014, 66, 444-454.
D. S. Li, H. Garmestani, S. Ahzi. Processing Path Optimization to Achieve Desired Texture for Polycrystalline Materials. Acta Materialia, 2007, 55, 647
D. S. Li, H. Garmestani, B. L. Adams. A Processing Path Model for Texture Evolution in Cubic-Orthotropic Polycrystalline System. International Journal of Plasticity, 2005, 21, 1591.
Sakai T, Saito Y, Matsuo M, Kawasaki K. Inhomogeneous texture formation in high speed hot rolling of ferritic stainless steel. ISIJ International, 1991; 31: 86-94.
Observation and modeling of the through-thickness texture gradient in commercial purity aluminum sheets processed by accumulative roll-bonding. Acta Materialia, 2010; 58: 1317-1331.
Kim S H, You B S, Yim, C D, Seo Y M. Texture and microstructure changes in asymmetrically hot rolled AZ31 magnesium alloy sheets. Materials Letters, 2005; 59: 3876-3880.
PeÂrocheau F, Driver J H. Texture gradient simulations for extrusion and reversible rolling of FCC metal. International Journal of Plasticity, 2000; 16: 73-89.
Pilchak A L, Li J, Sha G F, Groeber M, Tucker J and Rokhlin S. A quantitative assessment of microtexture in titanium alloys using destructive and nondestructive methods. Microscopy and Microanalysis, 2014; 20: 1448-1449.

BACKGROUND OF THE INVENTION

Field of the Invention

The present invention generally relates to a new system, method and computer programs to visualize texture heterogeneity of polycrystalline aggregate by macrotexture map with each color representing a set of texture (crystal orientation distribution). Each pixel/vector in macrotexture map represents a polycrystalline aggregate, with color defined by the local texture.

Background

Texture stands for preferred crystal orientation distribution, an important microstructure feature that determine the effective anisotropic properties, including thermal, mechanical, magnetic, and physical properties. Texture heterogeneity is a critical phenomenon observed in polycrystalline materials including metallic, ceramic and semicrystalline polymers. There is no representation method to visualize texture heterogeneity although the importance of texture heterogeneity has already been realized by the community.

Orientation of a single crystal is defined based on the rotation operation between the crystal coordinate system and the reference (sample) coordinate system. There are many representation methods for crystal orientation: Euler angles, Miller indices (hkl)<uvw>, rotation matrix Q, two pole angles $\alpha$ and $\beta$, etc. The most popular method is using Euler angles. Depending on the rotation sequence, there are several types of Euler angle notations. One of the most popular Euler angle notation is proposed by Bunge as $\phi_1, \phi, \phi_2$. This definition has been applied in Electron Backscatter Diffraction (EBSD) imaging software packages, like EDAX (TSL). When the crystal orientation is represented by polar angles, it is projected as a point in a stereographic projection map in pole figures.

For a polycrystalline aggregate composed by many crystals, texture (preferred distribution of crystal orientation), is defined as f(g). If the orientation g is represented by Euler angles, then:

$$f(g)=f(\varphi_1,\varphi,\varphi_2)$$

If crystals in the investigated polycrystalline aggregate are oriented uniformly in an orientation space G, then this aggregate has random texture. If the crystal orientation is not uniformly distributed, then the aggregate has preferred texture. Texture is observed in most engineering materials, minerals, and rocks, due to their thermomechanical history. There are many ways to visualize texture. For example, as a function of orientations represented by three Euler angles, texture is visualized as orientation distribution function plots. For example, when orientation g is defined as a point in stereographic projection map, texture is visualized as discrete or continuous pole figures and inverse pole figures.

Texture definition is based on the assumption that the material is homogeneous. It may stand true for small sample with limited number of crystals. It is also true for homogenized large sheet which has been heat treated at high temperature for long time (solution treatment) to eliminate the influence of previous thermomechanical history. However, it is not this case for large engineering parts, which are forged, rolled, stamped or quenched. Local specific plastic deformation due to thermal gradient and strain gradient introduced different texture for different locations. These difference will not be eliminated by further heat treatment since the preferred properties shall not be removed by follow up heat treatment process. The texture heterogeneity, or texture distribution are observed in rolled titanium sheets, forged airplane engine rotors, heat treated steel parts, etc. Traditionally, the microstructure of these parts/sheets is represented by a "typical" micrograph and the property is defined by a single number. With the development of probabilistic modeling, uncertainty quantification and mesoscale simulation, it is necessary to move forward into understanding of texture heterogeneity.

The tools and apps developed from this invention will be indispensable in study of texture heterogeneity, raising early alarms on critical signals in microstructure distribution, property distribution, high risky spot identification, risk management, etc. When utilized by large population, the methods and tools from this invention will provide deeper and more comprehensive understanding of the complexity of microstructure. They will guide building the bridges among microstructure, property and processing.

SUMMARY OF THE INVENTION

This section summarizes some aspects of the present invention and briefly introduces some preferred embodiments. Simplifications or omissions in this section as well as in the abstract or the title of this description may be made to avoid obscuring the purpose of this section, the abstract and the title. Such simplifications or omissions are not intended to limit the scope of the present invention.

One embodiment is method for visualizing texture heterogeneity by a macrotexture map, where a color code is defined by a texture parameter set representing local textures. Texture is distribution of crystal orientation. Texture heterogeneity is distribution of texture.

According to one aspect of the present invention, the invention is a system, method and computer program for visualizing texture heterogeneity by macrotexture map, where a color code is defined by texture parameter sets representing local textures.

In embodiments, the parameter set comprises weights of texture components used to express local textures. In embodiments, the texture parameter set comprises texture components including peak components, fiber components, random texture, and user defined textures.

In some cases, the parameter set is determined by weights of the features constructed by principal component analysis (PCA) of texture. In certain cases, the parameter set is determined by weights of the features constructed by cluster analysis of texture. In embodiments, the parameter set is determined by weights of the features constructed by spectral analysis of texture. In some cases the parameter set is determined by coefficients of spherical harmonics used in expansion expression of texture. In embodiments, the parameter set comprises coefficients of Fourier expansion of texture.

In some cases, the color code utilizes 1 or more numbers determined from the parameter set to create a color system. The color code may utilize one number of parameter sets to create the color system, including a gray bar, a jet color map, and a hot color map. The color code may utilize 2 or more number of parameter sets to create the color system. The color code may utilize reduced dimension of parameter sets to create the color system.

Another embodiment described herein is a method for generating an image of a polycrystalline component in the form of a macrotexture map comprising: obtaining a component; evaluating the polycrystalline structure of the component preliminarily; creating a sampling strategy to measure texture heterogeneity of at least one full side of the component; selecting a plurality of sampling locations on the at least one full side of the component for texture measurement; and selecting a texture measurement method. The method further includes using the selected texture measurement method to obtain data representing texture, wherein texture is based on crystal orientation distribution of aggregated crystals; processing the data representing texture to obtain a texture parameter set; and visually representing texture at different locations on the at least one full side of the component on a macrotexture map using the texture parameter set.

According to yet another embodiment, this invention is a method and system for evaluating, characterizing, representing and visualizing texture heterogeneity in polycrystalline aggregate, comprising:
evaluating polycrystalline component preliminarily, creating sampling strategy and selecting sampling locations, sizes and measurement methods;
characterizing textures at selected locations based on sampling strategy;
selecting appropriate texture parameter sets; analyzing texture measurement data to retrieve texture parameter sets; representing texture at different locations;
creating uniform color legend based on texture parameter sets as a local function;
creating macrotexture map; rendering and visualizing macrotexture map.

According to yet another embodiment, this invention is a method to create tessellated mesh in polycrystalline part with texture heterogeneity. Color coding is defined based on texture parameter sets. Different texture and properties are assigned to meshes with different color.

Figure 1:
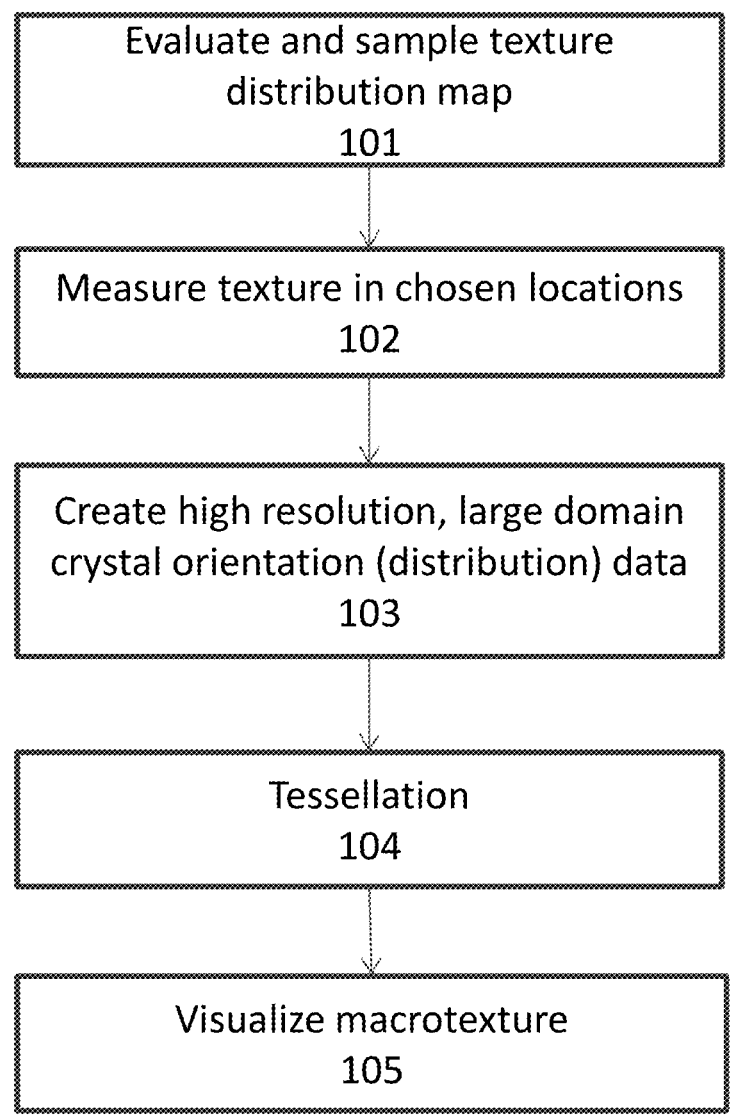
FIG. 1 shows a process of analyzing, characterizing, representing and visualizing texture heterogeneity in polycrystalline aggregate.

In the following detailed description, reference is made to the accompanying drawings, which form a part hereof, and in which is shown by way of illustration, and not by way of limitation, specific embodiments in which the disclosure may be practiced. It is to be understood that other embodiments may be utilized and that changes may be made without departing from the spirit and scope of the present disclosure.

DETAILED DESCRIPTION OF EMBODIMENTS

The detailed description of the invention is presented largely in terms of procedures, steps, logic blocks, processing and other symbolic representations that directly or indirectly resemble the operations of data processing devices. These process descriptions and representations are typically used by those skilled in the art to most effectively convey the substance of their work to others skilled in the art.

Aspects of the present disclosure are described herein with reference to flowchart, data flow, equations, and/or block diagrams according to embodiments of the disclosure. It will be understood that each block of the flowchart, data flow, equations, block diagrams, and/or combination of them, can be implemented by computer program instructions. These computer program instructions may be provided to a processor of a general purpose computer, computer clusters, special purpose computer, or other programmable data processing apparatus, such that the instructions which execute via the processor of the computer or other programmable data processing apparatus, create means for implementing the function/acts specified in the flow chart, data flow, equations, block diagrams, and/or combination of them.

According to various aspects of the present disclosure, the evaluation, characterization, representation and visualization of macrotexture image (also referred to herein as macrotexture map) in materials with texture heterogeneity or texture gradient is carried out according to one or more approaches set out herein.

Numerous specific details are set forth in order to provide a thorough understanding of the present invention. However, it will become obvious to those skilled in the art that the invention may be practiced without these specific details on crystal orientation, texture and heterogeneity. In other instances, well known methods, procedures, components, and circuitry have not been described in detail to avoid unnecessarily obscuring aspects of the present invention.

Reference herein to "one embodiment" or "an embodiment" means that a particular representation, method, definition, feature, or characteristic described in connection with the embodiment can be included in at least one embodiment of the invention. The appearances of the phrase "in one embodiment" in various places in the specification are not necessarily all referring to the same embodiment, nor are separate or alternative embodiments mutually exclusive of other embodiments. Further, the order of blocks in process flowcharts or diagrams representing one or more embodiments of the invention do not inherently indicate any particular order nor imply any limitations in the invention.

DETAILED DESCRIPTION OF THE EMBODIMENTS

The present invention pertains to generating an accurate and complete image of macrotexture in a large polycrystalline aggregate. In other words, the image provide information of geometric distribution of texture, or distribution of distribution of preferred crystal orientation.

FIG. 1 shows an embodiment of the invention in which how a macrotexture map (or macrotexture image or macrotexture graph) are evaluated, measured, represented and visualized. The step of sample texture distribution map 101 is the first crucial step to this embodiment. In this step, texture distribution in investigated samples is evaluated and a sampling strategy on texture distribution is chosen. If the sample is small enough to fully characterize within a reasonable time frame, then the sample can be characterized by a tiled EBSD scan, as in process 102. The tiles of EBSD images can be stitched together later in following process 103. Another exemplary approach is to utilize X-ray scan to measure texture in tile scan format. Sample vibration mode can be applied or not, depending on the size of the sample.

If the sample is large or high spatial resolution is required, then a limited number of locations in the sample will be chosen instead of a full scan without discrimination. For example, for a rolled sheet with texture gradient from the surface to the center, several sites along the sheet thickness will be selected to characterize the variance of texture against depth from surface. For example, for a forged turban engine fan blade, sample site density chosen in the areas with larger strain gradient and temperature gradient will be larger than sample density chosen in other areas. For example, for a quenched engine rotor, a calibrated FEM model will be used to simulate the strain and texture geometric distribution of the part. Then the sampling sites will be chosen based on the simulation results.

In process 102, texture will be measured on the sites chosen in process 101. There are many scattering and diffraction methods to measure texture. The most popular methods are EBSD for orientation image micrograph with local geometry information and X-ray Diffraction (XRD) for pole figures within a larger area. Other less popular methods include infrared diffraction and ultrasonic velocity measurement.

The collected texture measurement data at chosen sampling sites are passed into process 103. Data fusion is utilized to create a large domain high resolution texture image. The data point absent are interpolated using different algorithms. The large domain high resolution data set is passed into process 104 for further graphic rendering. Tessellation is performed in process 104 to divide the whole dataset into suitable structures for visualization. This criterion of mesh size is based on the gradient on both geometry and texture.

Tessellation structure is passed into process 105 with large domain high resolution dataset. Color coding and image visualization are performed in process 105. Macrotexture map is created and render in this last step. The detail of this process is illustrated in FIG. 2.

Figure 2:
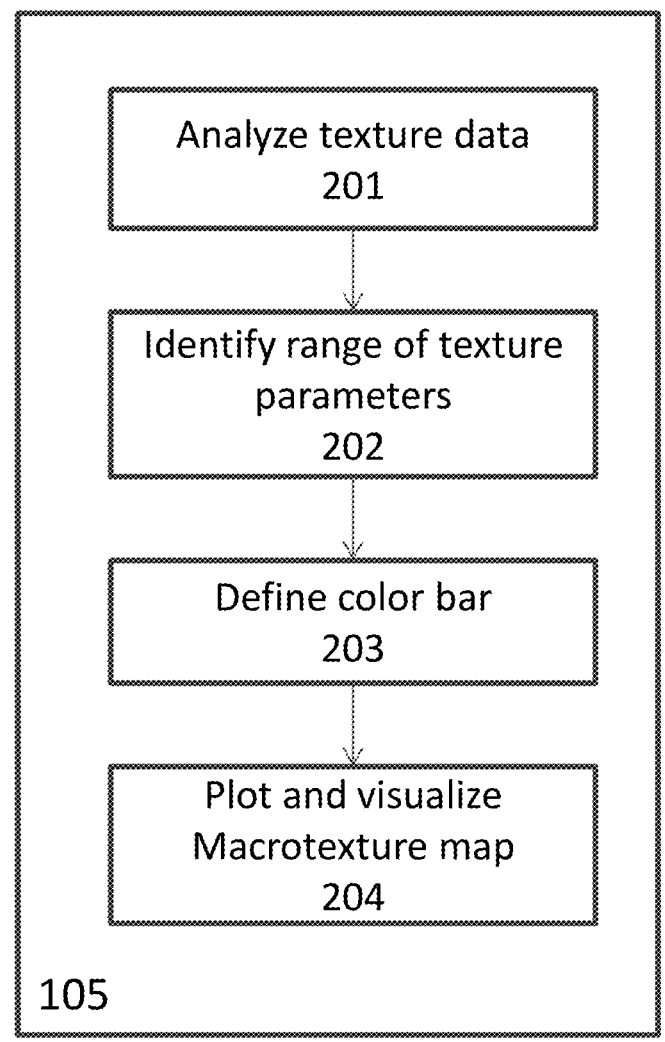
FIG. 2 shows a process of visualizing texture heterogeneity in macrotexture map using color bar based on texture representation.

FIG. 2 shows an embodiment of the invention in which how a macrotexture map (or macrotexture image or macrotexture graph) are represented and visualized. First step is texture analysis in process 201. In this step, texture data will go through dimension reduction from orientation distribution function (ODF) plot and pole figure format to a texture parameter set. Each set of texture data will be summarized into a parameter set. Each rendered image will use information of texture parameter set up to three dimensions. If interested variables in texture parameter set are more than 3, dimension reduction methods, such as cluster analysis, principal component analysis (PCA), classification, etc, will be utilized to reduce dimension. Rendered dimension size is limited due to the dimension limitation of color rendering in red green blue (RGB) color system with three number or gray scale with one number.

There are many methods to represent texture by a limited parameter set (or weight set). For example, a texture is represented as a summation of weighted orientation components:

$$f(g)=\Sigma_i w_i g_i$$

where $g_i$ are limited orientation components, and wi are corresponding weights. The set of weights here $[w_i]$ is used hereby to represent texture $f(g)$.

For example, a texture is represented as a summation of weighted texture components:

$$f(g)=\Sigma_i w_i f_i(g)$$

where $f_i(g)$ are limited texture components, and $w_i$ are corresponding weights. The set of weights here $[w_i]$ is used hereby to represent texture $f(g)$.

For example, a texture is represented by texture component method, where $$f(g)=F+\Sigma_i w_i f_i(g)$$

with $F+\Sigma_i w_i=1$ and $\oint_G f_i(g)dg=1$

Here F is the volume fraction of crystallites with random texture and $w_i$ is volume fraction for crystallites with texture $f_i(g)$ in orientation space G. The volume fraction $[F, w_i]$ is used hereby to represent texture $f(g)$.

For example, a texture is represented by supervised and unsupervised principal component analysis:

$$f(g)=\Sigma_i w_i k_i(g)$$

where $k_i(g)$ are principal components, and $w_i$ are corresponding scores or weight. The set of scores $[w_i]$ is used hereby to represent texture $f(g)$.

For example, a texture is represented by the norm of this distribution function:

$$n = \textstyle\int f(g)^2 dg$$

where n is norm of the distribution function. The norm n is used hereby to represent texture $f(g)$.

For example, a texture is represented by a series expansion of generalized spherical harmonics:

$$f(g) = \Sigma_{l=0}^{\infty} \Sigma_{m=-l}^{l} \Sigma_{n=-l}^{l} C_l^{mn} F_l^{mn}(g)$$

where $F_l^{mn}$ is spherical harmonics with order l, and $C_l^{mn}$ is coefficient of the corresponding spherical harmonics. The set of coefficients $[C_l^{mn}]$ is used hereby to represent texture $f(g)$.

Bunge's notation of Euler angles on orientation representation is used above. When Roe's notation is used, the expansion formula of texture is expressed as following:

$$f(g) = f(\Psi, \theta, \Phi) = \Sigma_{l=0}^{\infty} \Sigma_{m=-l}^{l} \Sigma_{n=-l}^{l} W_l^{mn} Z_l^{mn}(\cos\theta) e^{-im\Psi} e^{-in\Phi}$$

where $W_l^{mn}$ are the series coefficients and $Z_l^{mn}(\cos\theta)$ are a generalization of the associated Legendre functions, the so-called augmented Jacobi polynomials. The set of coefficients $[W_l^{mn}]$ is used hereby to represent texture $f(g)$.

There are other methods to represent textures, like vector method developed by Rue and Baro, the arbitrary defined cells (ADC) method developed by Pawlik, etc, dimension reduction, and cluster analysis. The weights or coefficients used in these expression composes a texture parameter set to represent texture.

In process 201, texture is analyzed and the local texture parameter sets are obtained. In process 202, these parameters sets for all the voxels/pixels in the macrotexture map will be investigated. The range of all the individual parameters are identified as well as the distribution density.

In process 203, color bar will be defined based on the information generated from process 202. The range will be used in process 203 to decide the maximum and minimum value of the color bar. The distribution density will be used to decide what kind of scale of the color bar will be used: linear scale or logarithm scale, the number of interval, etc.

Color coding is performed in process 203 to create appropriate color legend/bar for the purpose of representing macrotexture map. In EBSD map, a color is assigned for each possible orientation. One exemplary color code method used in EBSD map utilizes Euler angles $[\varphi_1, \phi, \varphi_2]$ representing crystal orientation. Three values in RGB vector are defined from the three Euler angles. Similarly, in macrotexture map a color is assigned to each texture, not orientation, in an element/pixel for macrotexture map. There are many ways to define color in macrotexture map. Generally, the following guidance is followed in color code definition:
1. Areas with same texture have same color.
2. Different color represents different texture
3. Similar color represents similar texture
4. The whole color space shall be utilized to reach full contrast.
5. If the range of textures investigated are concentrated in a limited region, the color space shall be exhausted by this region.

In the last process 204, the macrotexture map is plot and visualized. The graph is rendered according to the color bar/legend defined in process 203 and the macrotexture data generated in process 202.

Figure 3:
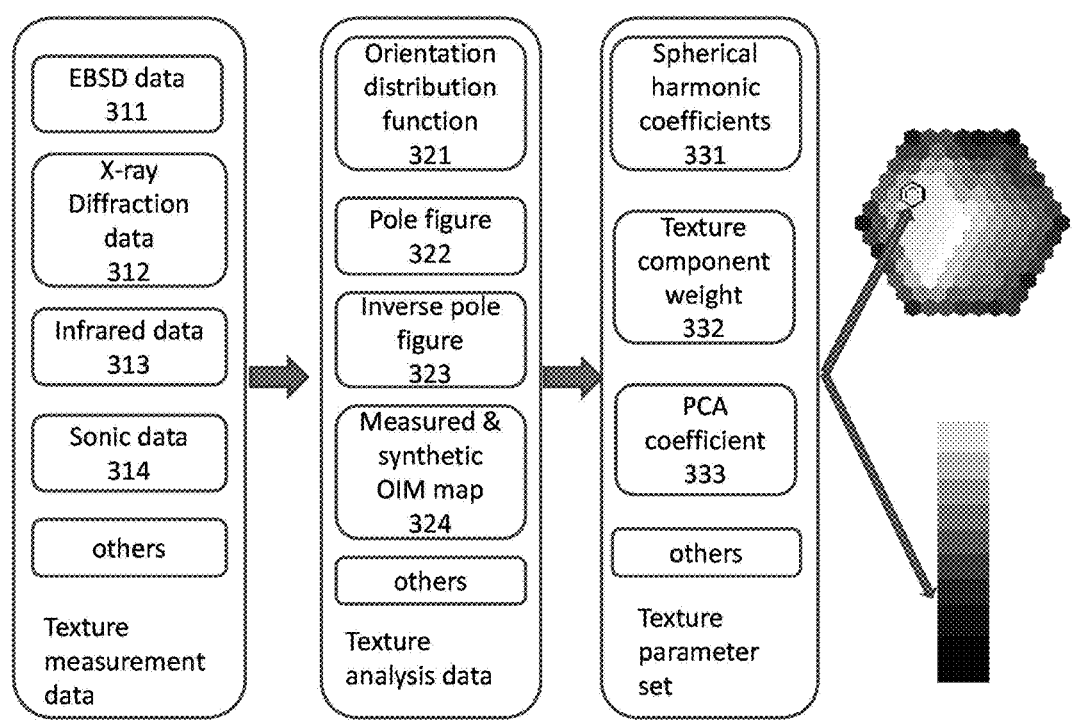
FIG. 3 shows data flow from texture measurement to analysis to parameter set to color bar definition.

FIG. 3 shows an embodiment of the invention to represent the dataflow in FIG. 1. First, texture of the polycrystalline aggregate is measured, using different facilities like EBSD, XRD, infrared, or ultrasonic method. The measurement data in the left column is passed into the second column to be analyzed to retrieve texture data at different locale. Texture is represented in statistical texture data in format of pole figures, inverse pole figures, orientation distribution function (ODF) plots, or in geometric texture data in format of orientation imaging map (OIM). These analyzed texture data is further analyzed to retrieve texture parameter set for color code purpose. Texture parameter set is in the format of spherical harmonics coefficients, texture component set weight, principal component analysis (PCA) scores, etc. The texture parameter set in the third column is used to determine the color of the texture in the locale in macrotexture map. If the number set has only one number, a gray scale will be used. If the number set has up to three numbers, a color scale (RGB or other rendering system) will be used. If the number set has more than 3 numbers, 3 of them will be selected or reduced dimension will be utilized.

EXAMPLES

Example 1

Figure 4:
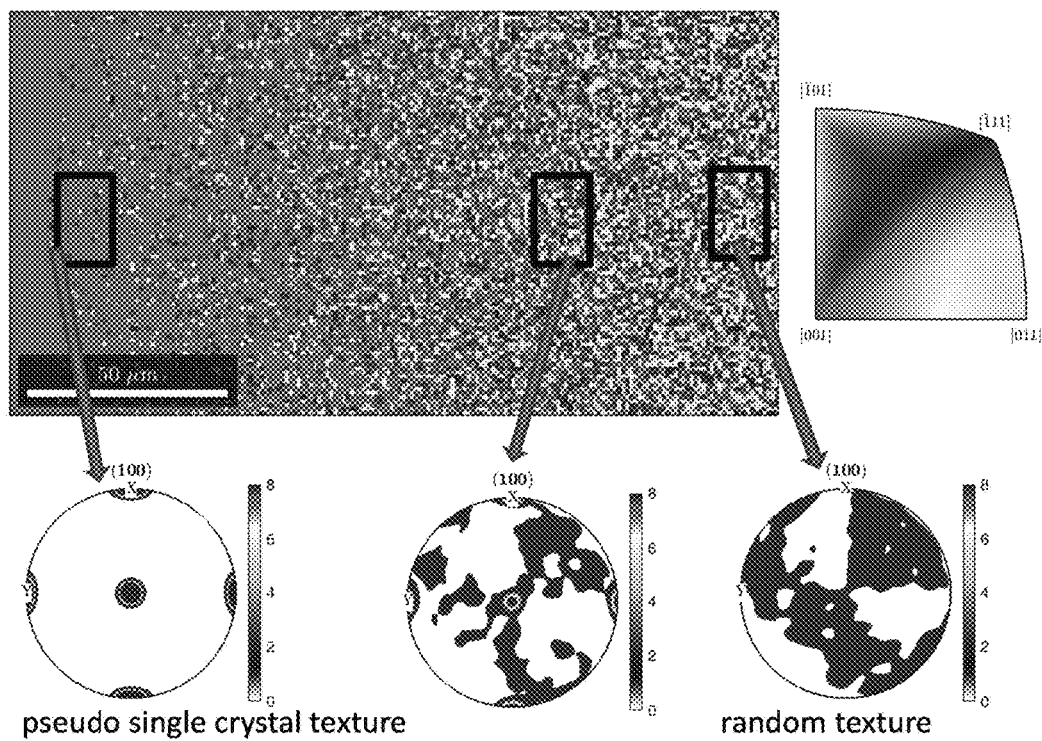
FIG. 4 shows an exemplary EBSD micrograph with texture gradient from a strong pseudo single crystal texture on left to random texture on right.

This shows how a polycrystalline aggregate with texture gradient is represented by macrotexture map. FIG. 4 illustrates an EBSD map of an aluminum sample with random texture on the right and (001)<100> pseudo single crystal configuration on the left. (001) pole figures in the locales of the left, middle and right are shown below the EBSD map. The pole figures demonstrated the strong texture on the left, random texture on the right and the gradient transition in the middle.

Figure 5:
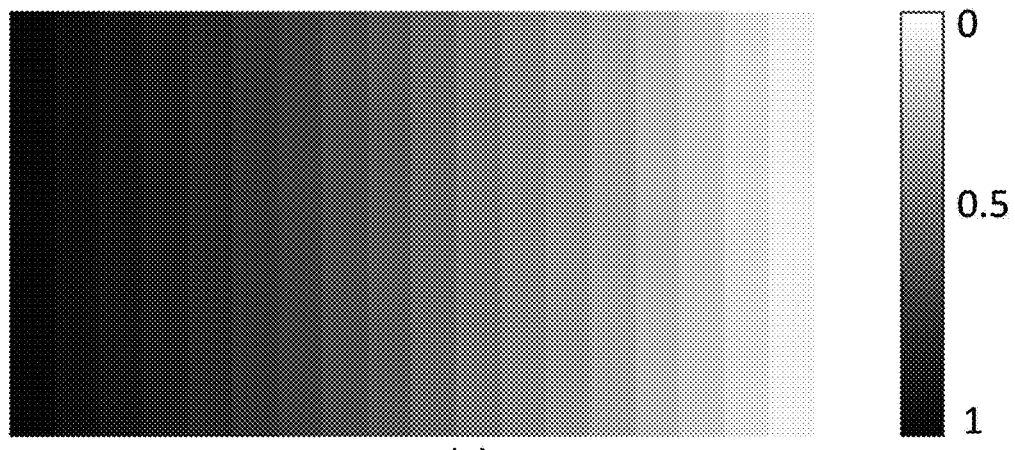
FIG. 5 shows macrotexture map of EBSD micrograph from FIG. 4 (a) in color bar and (b) in gray bar.
Figure 5:
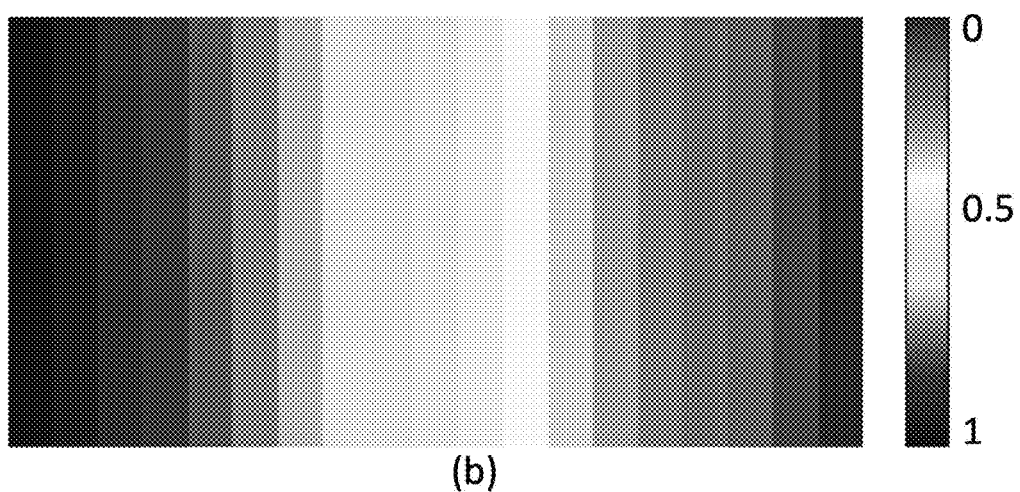

FIG. 5 illustrates a macrotexture map based on the EBSD map in FIG. 4 in gray bar, shown in FIG. 5a, and in jet color map, shown in FIG. 5b. Texture $f(g, \vec{x})$, in FIG. 4 is a locale function of location $\vec{x}$, expressed as below:

$$f(g, \vec{x}) = a(\vec{x}) f_1(g) + (1 - a(\vec{x})) f_2(g)$$

where $f_1(g)$ is pseudo single crystal texture, $f_2(g)$ is random texture and $a(\vec{x})$ is local texture component weight of $f_1(g)$.

$$f_1(g) = \begin{cases} 1 & \text{when } g = (001)(100) \\ 0 & \text{else} \end{cases}$$

$$f_2(g) = f_2(\varphi_1, \varphi, \varphi_2) = \frac{1}{8\pi^2 \cos\varphi}$$

FIG. 5 uses texture component weight/intensity $a(\vec{x}i)$ in color code. The top figure, FIG. 5a, uses $a(\vec{x})$ in gray scale and bottom figures uses $a(\vec{x})$ in jet colormap. The texture component weight $a(\vec{x})$ decreases from 1 on the left to 0 on the right.

Example 2

Figure 6:
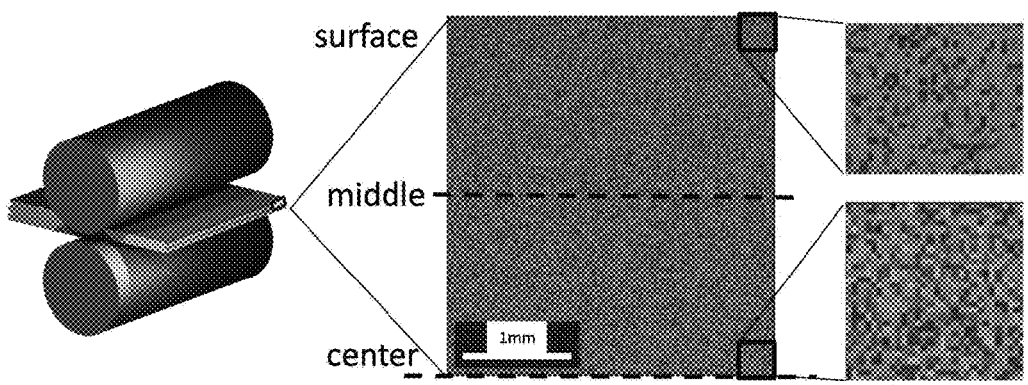
FIG. 6 shows an exemplary EBSD micrograph of a cross section of rolled aluminum sheet with texture gradient.

This shows how to represent a rolled sheet with texture heterogeneity using macrotexture map. All metal sheet demonstrates texture heterogeneity after forming process, like rolling, stamping and forging. The texture on the surface differentiates from the texture in the center of the rolled sheet even though the as-received sheet has uniform texture before rolling. In most cases, the followed heat treatment will not remove texture heterogeneity. FIG. 6 shows a part of EBSD map of a cross section of a rolled aluminum sheet. The magnified EBSD maps of the surface and the center areas are illustrated in the right column of FIG. 6.

Figure 7:
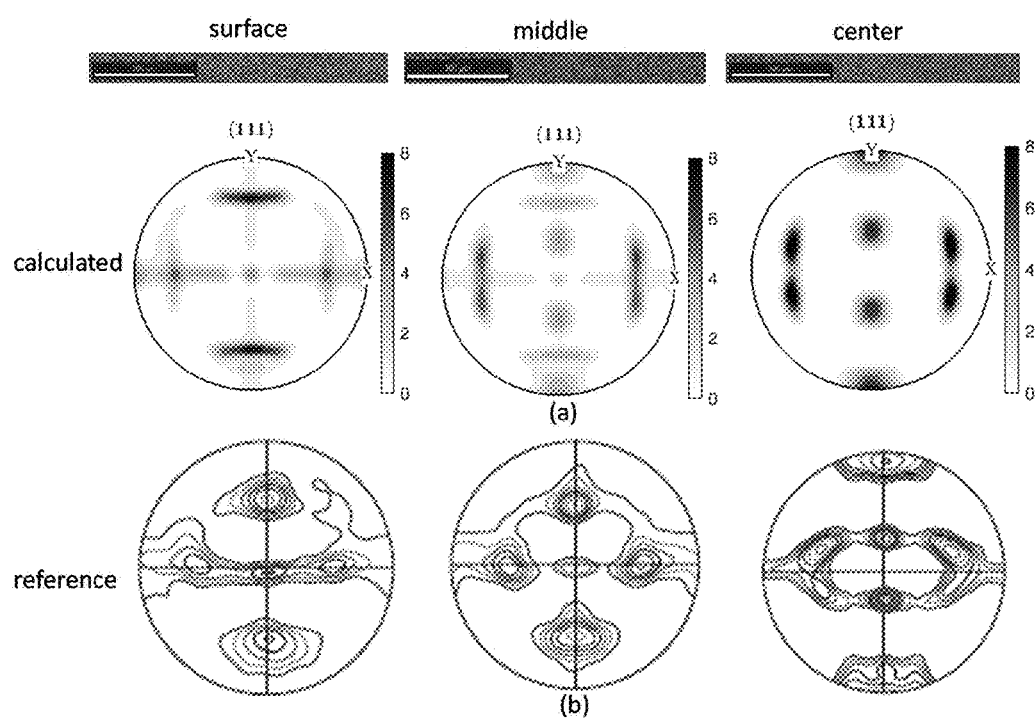
FIG. 7 shows partial EBSD micrographs, pole figures of different locations of a cross section of a rolled aluminum sheet from FIG. 6, comparing with the pole figures from literature (Li's work).

Statistical texture data obtained from different locales of the cross section of rolled aluminum sheet are demonstrated in format of (001) pole figures in the upper row of FIG. 7. EBSD maps from the surface, middle and center areas in FIG. 6 are used for pole figure calculation. Calculated Pole figures clearly demonstrated that the texture in surface area is very different from that at the center area. Texture evolves along the depth of the rolled sheet. Pole figures in lower rows of FIG. 7 are pole figures from different locations of rolled aluminum sheets measured by Li et. al. (Acta Materialia, 2010; 58: 1317-1331). Calculated pole figures in top row obtained from FIG. 7 are very similar to the experimental pole figures in bottom rows.

Figure 8:
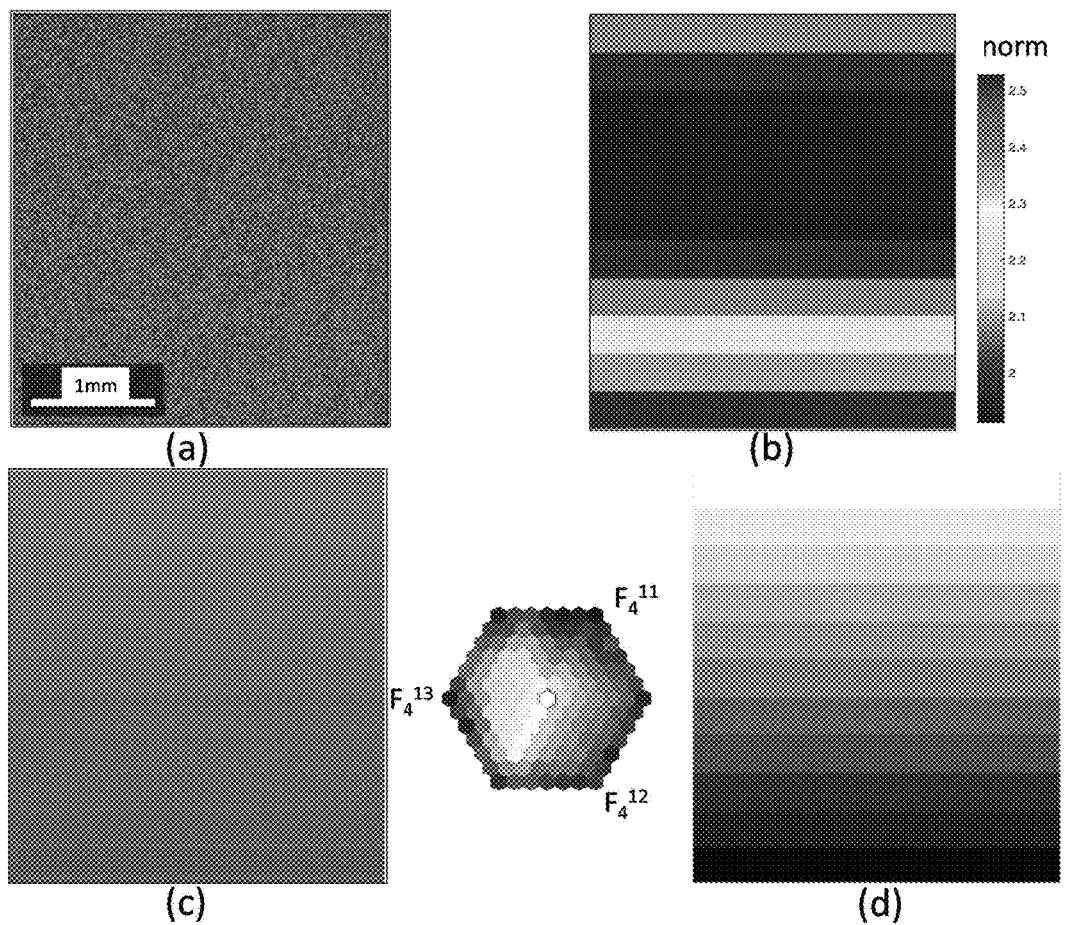
FIG. 8 shows (a) the exemplary EBSD micrograph, (b) a macrotexture map based on norm of texture, (c) a macrotexture map based on three Fourier coefficients, (d) a macrotexture map based on texture component intensity

Macrotexture maps of the cross section using different texture parameter sets are illustrated in FIG. 8. The original EBSD map is shown in FIG. 8(a). Correlated macrotexture map using norm of texture for color code is illustrated in FIG. 8(b). Macrotexture map using spherical harmonics coefficients $F_4^{11}$, $F_4^{12}$ and $F_4^{13}$ is illustrated in FIG. 8(c). Here color code is RGB color legend defined by the three spherical harmonics coefficients. Microstructure map using texture component coefficient, $a(\vec{x})$, is illustrated in FIG. 8(d). Here:

$$f(g, \vec{x}) = a(\vec{x})f_1(g) + (1-a(\vec{x}))f_2(g)$$

where $f_1(g)$ refers to the texture at the center of the rolled sheet and $f_2(g)$ refers to the texture at the surface of the rolled sheet. Since only one parameter is used in FIG. 8(d), a gray scale bar is utilized.

Example 3

Figure 9:
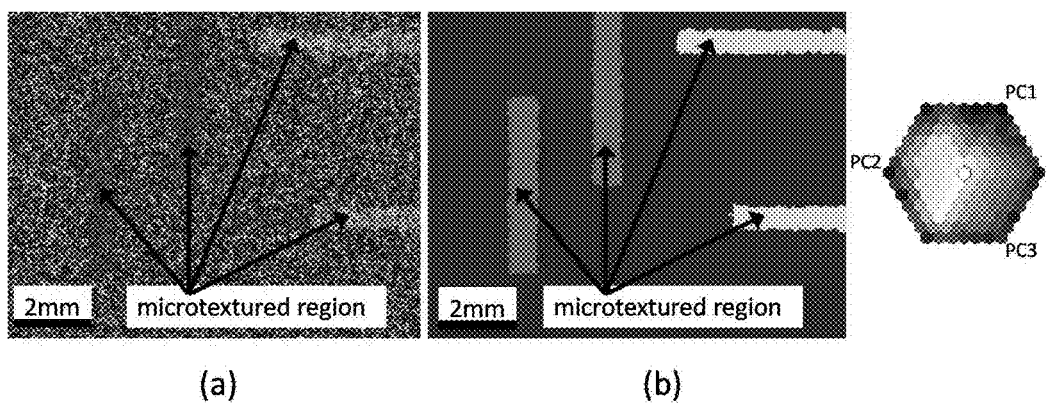
FIG. 9 shows (a) an exemplary EBSD micrograph with microtextured regions, (b) a macrotexture map based on principal component scores.

This shows how macrotexture map is used to capture microtextured regions in large sample. FIG. 9 (a) shows EBSD map of Ti64 with two kinds of microtextured regions. One kind of region has c-axis aligned along vertical direction; the other kind with c-axis aligned along horizontal direction. FIG. 9(b) shows macrotexture map using parameter set from principal component analysis. In this analysis, the first principal component PC1 is random texture; the other two principal component PC2 and PC3 are close to the two kinds of microtextured region. Macrotexture clearly demonstrates how these microtextured regions are merged in random matrix. Size, location, and geometric correlation of these microtextured regions are clearly demonstrated in FIG. 9(b).

Example 4

Figure 10:
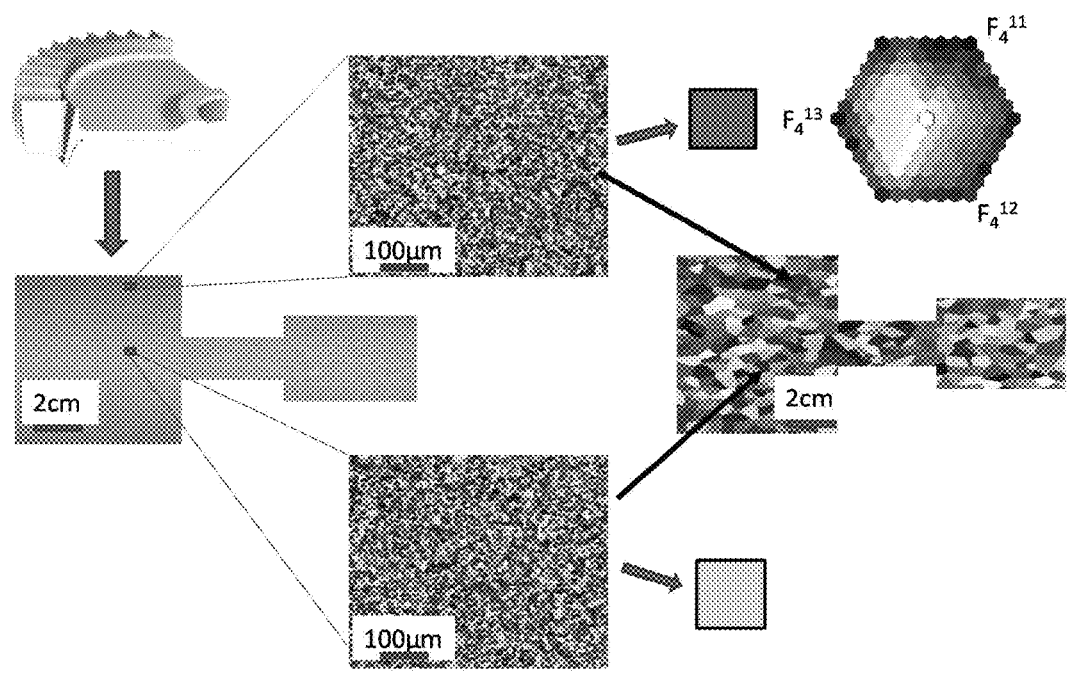
FIG. 10 shows a picture of large polycrystalline component, related local EBSD micrographs with corresponding macrotexture color defined from the Fourier coefficients, and tessellated macrotexture map of this component demonstrating texture heterogeneity.

This shows how macrotexture map is used to demonstrate texture heterogeneity in real world large components/parts with microstructure heterogeneity and how this will contribute to future modeling and simulation. This method is important for further study on property heterogeneity, related behavior uncertainty quantification and hot spot identification. FIG. 10 demonstrated a cross section of an airplane engine high pressure compressor rotor. This nickel superalloy rotor demonstrates texture heterogeneity due to high strain gradient during forging process and high temperature gradient during followed heat treatment. EBSD maps of two locations revealed different textures. Spherical harmonics coefficients from these EBSD maps determines the color of the location in macrotexture map. The same color legend as FIG. 9(c) is utilized here for macrotexture map. Voronoi tessellation has been used in meshing process for future finite element study. Each mesh is colored based on color legend generated from the Fourier coefficients, $F_4^{11}$, $F_4^{12}$ and $F_4^{13}$. Due to texture heterogeneity, each mesh with different texture will be assigned different properties.

I claim:

1. A method for generating an image of a polycrystalline component in the form of a macrotexture map comprising:
    obtaining a component;
    evaluating the polycrystalline structure of the component preliminarily;
    creating a sampling strategy to measure texture heterogeneity of at least one full side of the component;
    selecting a plurality of sampling locations on the at least one full side of the component for texture measurement;
    selecting a texture measurement method;
    using the selected texture measurement method to obtain data representing texture, wherein texture is based on crystal orientation distribution of aggregated crystals;
    processing the data representing texture to obtain a texture parameter set, wherein the texture parameter set comprises one of:
    weights of texture components used to express local texture, and random texture; and
    visually representing texture at different locations on the at least one full side of the component on a macrotexture map using the texture parameter set by
        creating a uniform color map based on the texture parameter set as a local function;
        creating the macrotexture map based the color map; and
        rendering the macrotexture map.

2. The method as recited in claim 1, wherein the parameter set is determined by weights of the features constructed by principal component analysis (PCA) of texture.

3. The method as recited in claim 1, wherein the parameter set is determined by weights of the features constructed by cluster analysis of texture.

4. The method as recited in claim 1, wherein the parameter set is determined by weights of the features constructed by spectral analysis of texture.

5. The method as recited in claim 1, wherein the parameter set is determined by coefficients of spherical harmonics used in expansion expression of texture.

6. The method as recited in claim 1, wherein the parameter set comprises coefficients of Fourier expansion of texture.

7. The method as recited in claim 1, wherein a color code utilizes 1 or more numbers determined from the parameter set to create a color system.

8. The method as recited in claim 7, wherein the color code utilizes one number of parameter sets to create the color system, including a gray bar and a jet color map.

9. The method as recited in claim 7, wherein the color code utilizes 2 or more number of parameter sets to create the color system.

10. The method as recited in claim 7, wherein the color code utilizes reduced dimension of parameter sets to create the color system.

11. The method as recited in claim 1, wherein the macrotexture map is a colored map with a first texture represented by a first color and a second texture represented by a second color.

12. The method of claim 1, wherein the polycrystalline component is a metal sheet.

* * * * *